US009415362B2

(12) United States Patent
Stoyanov et al.

(10) Patent No.: US 9,415,362 B2
(45) Date of Patent: Aug. 16, 2016

(54) PROCESS AND APPARATUS FOR PRODUCING A TABLETTING AID AND ALSO A TABLETTING AID AND TABLETTING MIXTURE

(75) Inventors: Edmont Stoyanov, Aalen (DE); Reinhard Vollmer, Windesheim (DE); Tobias Götz, Rosenberg (DE)

(73) Assignee: J. Rittenmaier & Sohne GmbH & Co. KG, Rosenberg (DE)

( * ) Notice: Subject to any disclaimer, the term of this patent is extended or adjusted under 35 U.S.C. 154(b) by 1118 days.

(21) Appl. No.: 12/867,925

(22) PCT Filed: Mar. 13, 2009

(86) PCT No.: PCT/EP2009/001872
§ 371 (c)(1),
(2), (4) Date: Aug. 17, 2010

(87) PCT Pub. No.: WO2009/112287
PCT Pub. Date: Sep. 17, 2009

(65) Prior Publication Data
US 2011/0013476 A1    Jan. 20, 2011

(30) Foreign Application Priority Data
Mar. 14, 2008    (DE) .......................... 10 2008 014 237

(51) Int. Cl.
*A61K 9/20* (2006.01)
*A61K 9/14* (2006.01)
*B01J 2/16* (2006.01)
*A61K 47/38* (2006.01)

(52) U.S. Cl.
CPC ................. *B01J 2/16* (2013.01); *A61K 9/2095* (2013.01); *A61K 47/38* (2013.01)

(58) Field of Classification Search
CPC ... A61K 9/2077; A61K 9/2095; A61K 31/00; A61K 9/14; A61K 9/1605; A61K 47/38; A61J 3/10; Y10S 514/951; Y10S 514/96; B01J 2/16
See application file for complete search history.

(56) References Cited

U.S. PATENT DOCUMENTS

| | | | | |
|---|---|---|---|---|
| 4,753,803 A | * | 6/1988 | Klug et al. | 424/474 |
| 5,006,345 A | * | 4/1991 | Lang | A61K 9/2018 424/467 |
| 5,041,430 A | * | 8/1991 | Addicks et al. | 514/161 |
| 5,840,769 A | * | 11/1998 | Kolter | A61K 9/2027 514/772.5 |
| 5,948,437 A | * | 9/1999 | Parikh et al. | 424/464 |
| 6,319,519 B2 | * | 11/2001 | Woolfe et al. | 424/472 |
| 6,509,036 B2 | * | 1/2003 | Pather et al. | 424/466 |
| 6,528,096 B1 | * | 3/2003 | Musa | A61K 9/0075 424/400 |
| 6,645,961 B1 | * | 11/2003 | Lui et al. | 514/231.5 |
| 6,780,508 B1 | * | 8/2004 | Caponetti | A61K 9/0075 424/434 |
| 7,067,149 B1 | * | 6/2006 | Chauveau | A61K 9/0056 424/464 |
| 8,337,816 B2 | * | 12/2012 | Brown | A61K 9/0075 424/46 |
| 2005/0031683 A1 | * | 2/2005 | Kapoor et al. | 424/464 |
| 2007/0137561 A1 | | 6/2007 | Osako et al. | |
| 2007/0148249 A1 | * | 6/2007 | Franc | A61K 9/2095 424/489 |
| 2007/0275057 A1 | * | 11/2007 | Shawer | A61K 9/2018 424/464 |

FOREIGN PATENT DOCUMENTS

| | | | |
|---|---|---|---|
| EP | 0 192 173 | 8/1986 | |
| EP | 0 819 429 | 1/1998 | |
| SE | WO 0013671 A1 * | 3/2000 | ........... A61K 9/2009 |
| WO | 00/13671 | 3/2000 | |
| WO | WO 2007062338 A2 * | 5/2007 | |

OTHER PUBLICATIONS

English language translation of Written Opinion in PCT/EP2009/001872.

* cited by examiner

*Primary Examiner* — Robert A Wax
*Assistant Examiner* — Olga V Tcherkasskaya
(74) *Attorney, Agent, or Firm* — Faegre Baker Daniels LLP

(57) ABSTRACT

The invention concerns a process for the production of a tableting excipient with the following process steps:
At least two of the following components are made available:
A filler/binding agent;
A lubricant;
A flow regulating agent;
A disintegrant;
The available components are mixed together.

14 Claims, 4 Drawing Sheets

Figure 1: Pressure diagram placebos – comparison
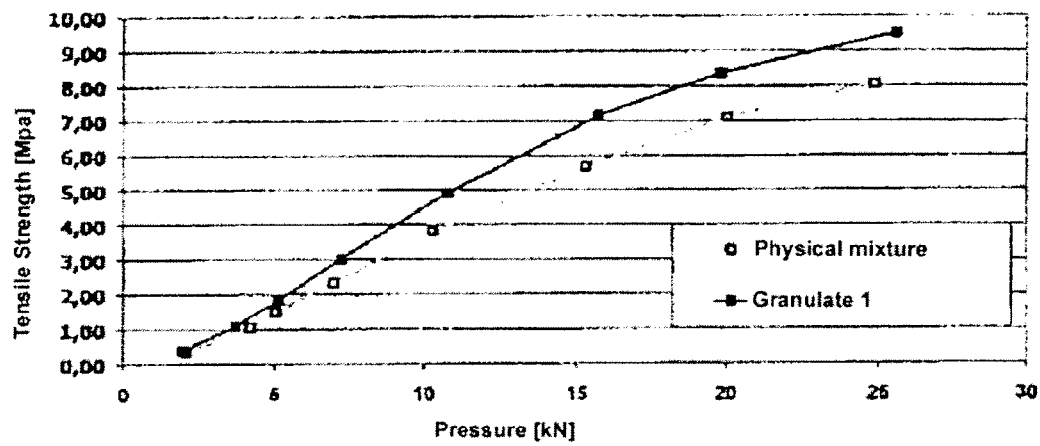
Figure 2: Ejection force placebos – comparison
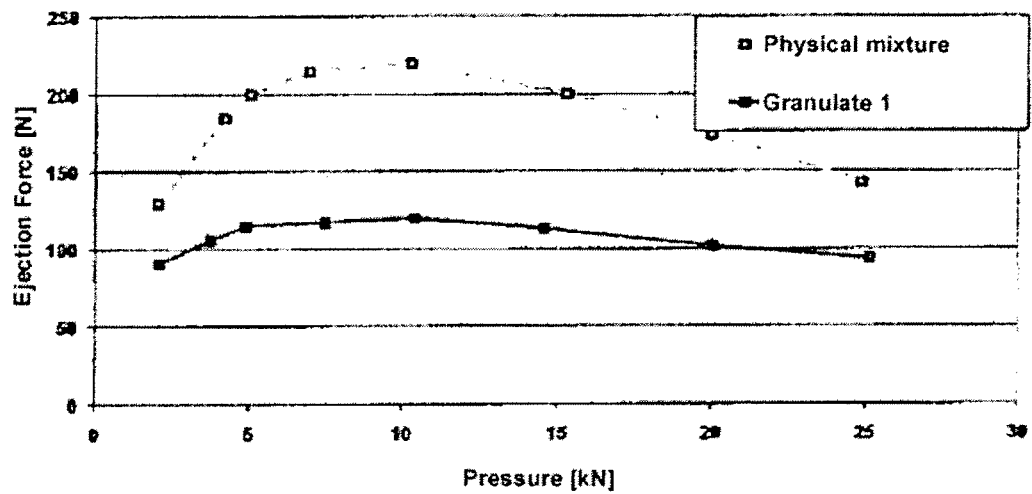

Figure 3: Pressure diagram 40 % paracetamol – comparison
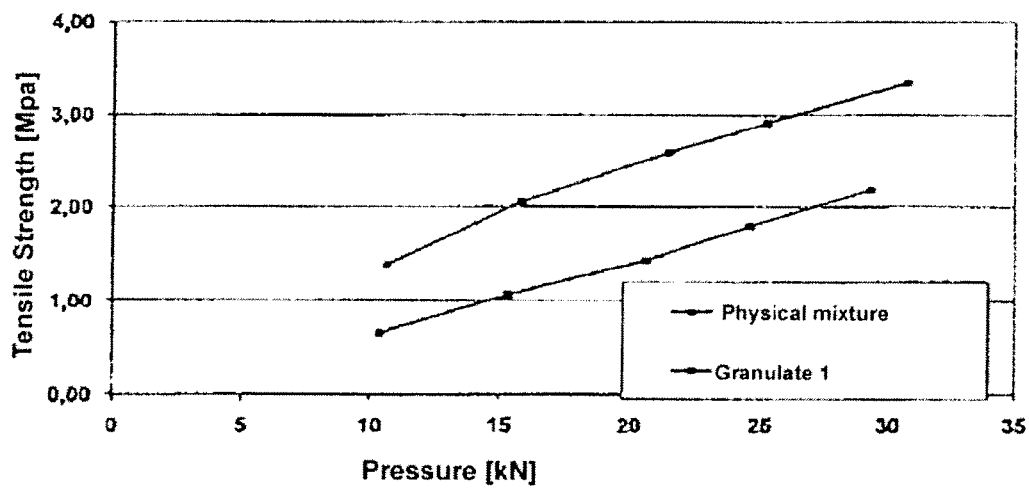
Figure 4: Ejection force 40 % paracetamol – comparison
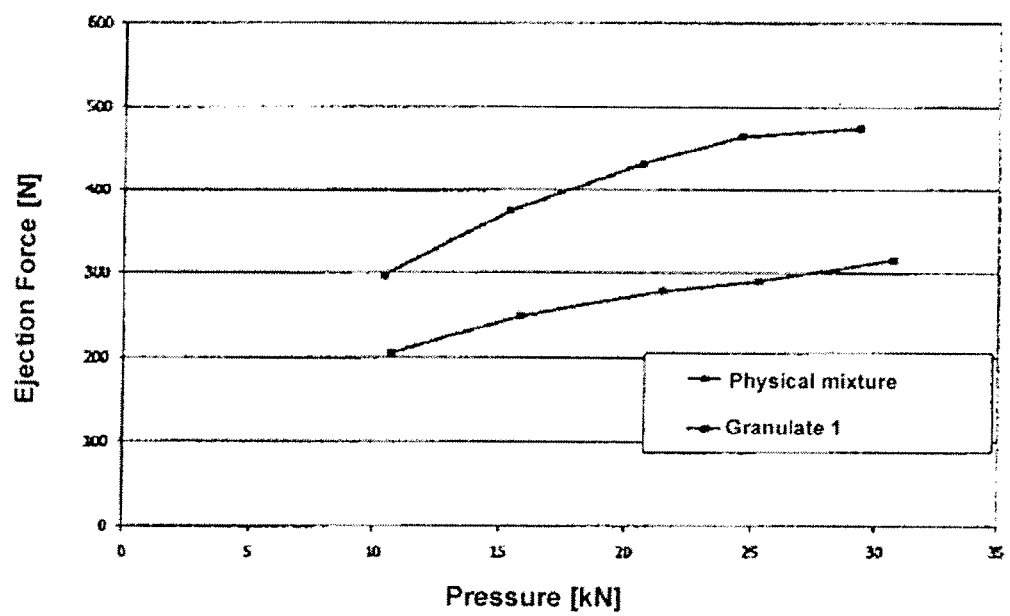

Figure 5: Compression diagram Enalapril – comparison
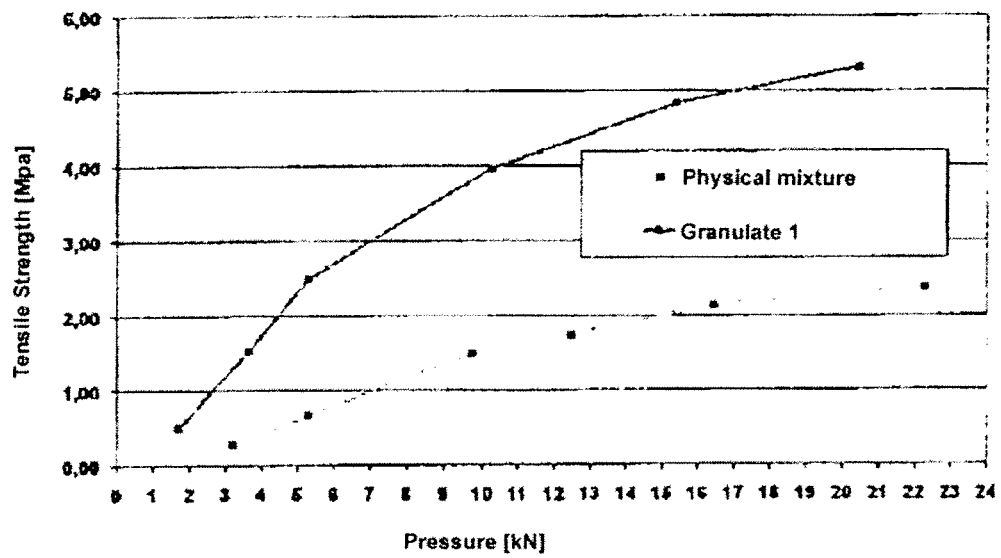
Figure 6: Ejection force Enalapril – comparison
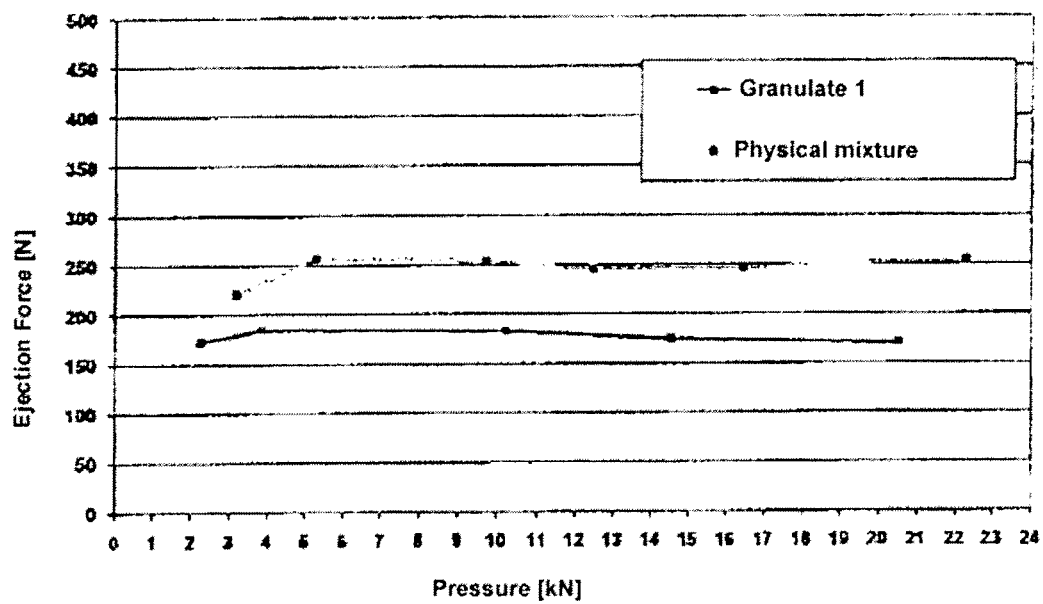

PROCESS AND APPARATUS FOR PRODUCING A TABLETTING AID AND ALSO A TABLETTING AID AND TABLETTING MIXTURE

CROSS-REFERENCE TO RELATED APPLICATION

This application is related to and claims the benefit under 35 U.S.C. §119 and 35 U.S.C. §365 of International Application No. PCT/EP2009/001872, filed Mar. 13, 2009, the disclosure of which is expressly incorporated herein by reference.

FIELD OF THE INVENTION

The invention concerns a process, a production means and the substances in accordance with the above title.

BACKGROUND

Direct compression is the most commonly used method for the production of tablets. The process consists of various mixing steps. First, the active substance and all excipients (mainly filler, binding agent and disintegrating agent) except the lubricants are mixed together. This can be accomplished in a single mixing step, whereby the filler, binding agent and disintegrating agent are combined with the active substance. Alternatively, numerous sequential mixing steps may be carried out. Subsequently, the lubricant is added to the mixture and in turn mixed with said. The result is a tabletting mixture. This is compressed in a tabletting press.

In pharmaceutical technology, combined excipients are available (direct tabletting excipients). These are combined tabletting excipients which consist of numerous individual substances (frequently filler, binding agent and disintegrating agents) which are produced by means of co-processing (for example spray drying, compaction or granulation). These multi-functional substances demonstrate certain advantages over the physical mixture of the individual components. See EP 0 819 429.

All known combinations of filler, binding agent and disintegrating agents contain no lubricant. There are various reasons for this, particularly the danger of over mixing, lower tablet hardness and coatings of the tablets.

SUMMARY

The invention has the fundamental object of providing a process as well as a device for production of a tabletting excipient and also a tabletting excipient as well as a tabletting mixture, primarily in order to obtain the following advantages:
Lower ejection forces after compressing the tablet mixture,
Good lubricant properties and good flow properties of the tablet mixture,
Sufficient hardness of the tablet,
Lower abrasion of the tablet,
Lower sensitivity to moisture.

This object shall be achieved through the characteristics of the independent claims.

BRIEF DESCRIPTION OF THE DRAWINGS

FIG. 1 is graph comparing tensile strength vs. pressure data for a placebo formula of a tabletting excipient (granulate 1) and a physical mixture of the individual components.

FIG. 2 is a graph comparing ejection force vs. pressure data for a placebo formula of a tabletting excipient (granulate 1) and a physical mixture of the individual components.

FIG. 3 is graph comparing tensile strength vs. pressure data for a paracetamol formula of a tabletting excipient (granulate 1) and a physical mixture of the individual components.

FIG. 4 is graph comparing ejection force vs. pressure data for a paracetamol formula of a tabletting excipient (granulate 1) and a physical mixture of the individual components.

FIG. 5 is graph comparing tensile strength vs. pressure data for an enalapril formula of a tabletting excipient (granulate 1) and a physical mixture of the individual components.

FIG. 6 is graph comparing ejection force vs. pressure data for an enalapril formula of a tabletting excipient (granulate 1) and a physical mixture of the individual components.

DETAILED DESCRIPTION

Figure 7:
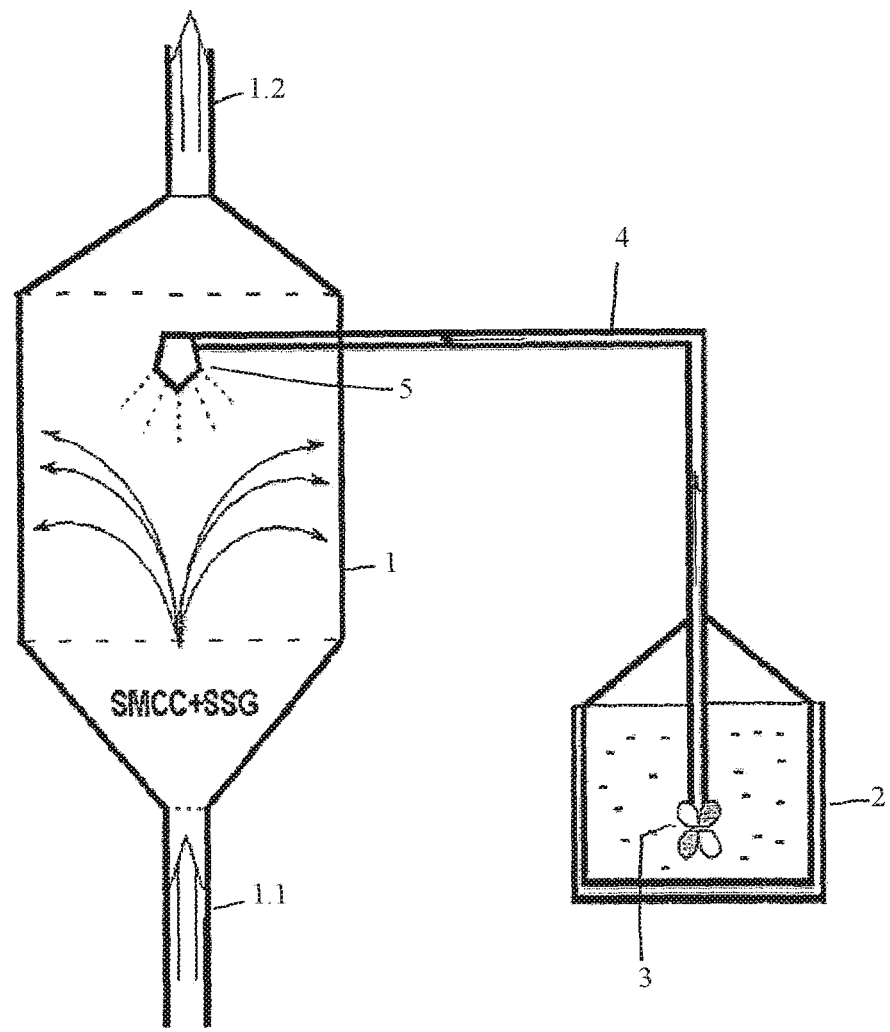
FIG. 7 is a device for executing the process of the present disclosure.

The tabletting excipient of the invention contains numerous individual substances; in general, a filler, a binding agent, a disintegrating agent and a lubricant. All of the specified substances thereby are combined in a single mixture; in this manner said mixture may be described as multi-functional. This has the major advantage that the user, or tablet producer, only needs to mix a finished mixture with the active substance of the tablet. In this manner, the dosing of individual tabletting excipients is eliminated, thereby reducing the processing costs and the problem of precision of the dosages of the individual tabletting excipients does not arise.

The invention results in the following additional advantages:
Significantly lower ejection forces due to the even distribution of the lubricant in the tablet and thereby a higher rate of tabletting or quicker production.
Lower concentrations of lubricant in the tablet are sufficient.
A better tablet hardness.
A better abrasion level, particularly with lower dosages of active substances.
Better flow properties of the tabletting compound.
A lower sensitivity to moisture.
No influence on the disintegration and release of the active substance.
No over-mixing or coating.
It requires only a mixing step with the active substance(s). This saves in production time and costs.
Lower dust level.

The production process of the mixture from the above specified components ideally is carried out by means of wet granulation in accordance with all of the known methods such as mixer granulation, perforated disk granulation, fluid bed granulation, extrusion or Shugi granulation.

For fluid bed granulation, for example, the following possibilities exist.
Variation A: Silicified microcrystalline cellulose and croscarmellose or sodium starch glycolate are located in the fluid bed and sprayed with a hot, aqueous solution of sodium stearyl fumarate at 30-97° C. The granulate is then dried in the fluid bed.
Variation B: Microcrystalline cellulose and croscarmellose or sodium starch glycolate are located in the fluid bed and sprayed with a hot, aqueous solution/suspension of sodium stearyl fumarate and silicon dioxide at 30-97° C. The granulate is then dried in the fluid bed.

Variation C: Microcrystalline cellulose, croscarmellose or sodium starch glycolate and silicon dioxide are located in the fluid bed and sprayed with a hot, aqueous solution of sodium stearyl fumarate at 30-97° C. The granulate is then dried in the fluid bed.

Variation D: Silicified microcrystalline cellulose is located in the fluid bed and sprayed with a hot, aqueous solution/suspension of sodium stearyl fumarate and croscarmellose or sodium starch glycolate. The granulate is then dried in the fluid bed.

Variation E: Microcrystalline cellulose is located in the fluid bed and sprayed with a hot, aqueous solution/suspension of sodium stearyl fumarate, croscarmellose or sodium starch glycolate and silicon dioxide at 30-97° C. The granulate is then dried in the fluid bed.

The particle size of the fluid bed granulate depends on the type of cellulose.

Another method for producing the new tableting excipient which can be direct compressed (DC) is the spray drying. All components are mixed in hot water and sprayed together. The particle size of the product depends on the type of cellulose and the spraying rate.

The tableting excipient of the invention containing some or all of the specified components, filler, binding agent, flow regulating agent, disintegrant and lubricant, is ideally produced through granulation in the fluid bed. Refer to the possible following variations A and B:

Variation A:

One places the Silicified microcrystalline cellulose (PROSOLV® SMCC 90, JRS Pharma) and sodium starch glycolate (EXPLOTAB®, JRS Pharma) in the fluid bed. The substances are heated to 30-97° C. and sprayed with a hot, aqueous solution of 0.3-6% sodium stearyl fumarate (PRUV®, JRS Pharma). The granulate is then dried in the fluid bed.

Variation B:

One places the microcrystalline cellulose (VIVAPUR® 102, JRS Pharma) and the sodium starch glycolate (EXPLOTAB®, JRS Pharma) in the fluid bed. The substances are heated to 30-97° C. and sprayed with a hot, aqueous suspension of 1-20% silicon dioxide (CabOsil M5®, Carbot or Aerosil®, Degussa) and 0.3-6% sodium stearyl fumarate (PRUV®, JRS Pharma). The granulate is then dried in the fluid bed.

The two variations result in granulates of the same quality. Table 1 shows four examples of granulates produced with the above processes.

TABLE 1

Examples of granulates

| # | Granulate 1 % | Granulate 2 % | Granulate 3 % | Granulate 4 % |
|---|---|---|---|---|
| Microcrystalline cellulose (VIVAPUR® 102) | 96.5 | 96.0 | 95.0 | 94.0 |
| Silicon dioxide (CabOsil M5®) | 2.0 | 2.0 | 2.0 | 2.0 |
| Sodium starch glycolate (Explotab®) | 1.0 | 1.5 | 2.0 | 3.0 |
| Sodium stearyl fumarate (PRUV®) | 0.5 | 0.5 | 1.0 | 1.0 |

Flow angle: 25-28°, flowability: 0.6-0.9 g/s with FloDex, 4 mm ring diameter, apparent density: 340-400 g/l, moisture: 4-6%.

EXAMPLES

The tableting excipient of the invention is placed in a placebo with the physical mixture of the individual components, a 40% paracetamol and compared with an enalapril formula. The results are shown in tables 2, 3 and 4.

Placebo tablets

| 100% DC tableting excipients* | vs. | Physical mixture ** | |
|---|---|---|---|
| (Granulate 1) | | Microcrystalline cellulose | 96.5% |
| | | Silicon dioxide | 2% |
| | | Sodium starch glycolate (Explotab®) | 1% |
| | | Sodium stearyl fumarate (PRUV®) | 0.5% |

*The tableting excipient of the invention is compressed alone with various pressures.
** All components except sodium stearyl fumarate (PRUV®) are mixed for 15 minutes. The lubricant is then added and mixed for an additional 3 minutes and then compressed with various pressures.

TABLE 2

Direct comparison between a tableting excipient (granulate 1) and a physical mixture of the individual components; Placebo formula

| Substance | Pressure [kN] | Tensile strength [MPa] | Ejection Force [N] | Abrasion [%] | Disintegration [s] |
|---|---|---|---|---|---|
| Granulate 1 | 10 | 5.0 | 120 | 0.31 | 10 |
| Physical Mixture | 10 | 3.9 | 220 | 0.76 | 10 |

The DC tableting excipient of the invention has significantly better compressibility and tablet hardness, lower ejection force and less abrasion than the physical mixture (table 2, FIGS. 1 and 2).

Paracetamol tablets

| 60% DC tableting excipients* | vs. | Physical mixture ** | |
|---|---|---|---|
| (Granulate 1) | | Microcrystalline cellulose | 57.9% |
| 40% Paracetamol | | Silicon dioxide | 1.2% |
| | | Sodium starch glycolate (Explotab®) | 0.6% |
| | | Paracetamol | 40.0% |
| | | Sodium stearyl fumarate (PRUV®) | 0.3% |

*The DC tableting excipient is mixed with the paracetamol for 15 minutes and then compressed at various pressures.
** All components except sodium stearyl fumarate (PRUV®) are mixed for 15 minutes. The lubricant is then added and mixed for an additional 3 minutes and then compressed at various pressures.

TABLE 3

Comparison between the tablet mixture which can be direct compressed (granulate 1) and the physical mixture of the various components; 40% paracetamol (PCM) formula

| Substance | Pressure [kN] | Tensile strength [Mpa] | Ejection Force [N] | Abrasion [%] | Disintegration [s] |
|---|---|---|---|---|---|
| Granulate 1 | 15 | 2.2 | 240 | 0.40 | 9 |
| Physical Mixture | 15 | 1.1 | 380 | 0.51 | 9 |

The PCM tablets with the new DC tableting excipient have significantly lower ejection forces and better abrasion for the same disintegration periods. Furthermore, the new substance requires 50% less pressure for the same tablet hardness in comparison with the physical mixture, which indicates a better compressibility (table 3, FIGS. 3 and 4).

| Enalapril tablets | | |
|---|---|---|
| 92.30% DC tableting excipients* vs. | Physical mixture ** | |
| (Granulate 1) 7.70% Enalapril | Microcrystalline cellulose | 89.07% |
| | Silicon dioxide | 1.85% |
| | Sodium starch glycolate (Explotab ®) | 0.92% |
| | Enalapril | 7.70% |
| | Sodium stearyl fumarate (PRUV ®) | 0.46% |

*The DC tableting excipient is mixed with the enalapril for 15 minutes and then compressed at various pressures.
** All components except sodium stearyl fumarate (PRUV ®) are mixed for 15 minutes. The lubricant is then added and mixed for an additional 3 minutes and then compressed at various pressures.

TABLE 4

Direct comparison of tableting excipient which can be direct compressed (granulate 1) with the physical mixture of the individual components; Enalapril Formula

| Substance | Pressure [kN] | Tensile strength [Mpa] | Ejection Force [N] | Abrasion [%] | Disintegration [s] |
|---|---|---|---|---|---|
| Granulate 1 | 15 | 4.0 | 180 | 0.04 | 19 |
| Physical Mixture | 15 | 1.6 | 260 | 0.04 | 26 |

The granulate formula has significantly better compressibility than the physical mixture (table 4, FIGS. 5 and 6). With the same pressure, the new tableting excipient has more than double tablet hardness (FIG. 5) and exhibits a 30% lower ejection force.

A device for executing the process of the invention is shown in FIG. 7. The device consists of the following components:

A container 1 serves to receive sodium starch glycolate and silicified microcrystalline cellulose. A fluid bed is formed from these two components. Refer to the air intake 1.1 and the air outlet 1.2.

A lubricant in liquid form, such as sodium stearyl formulate, is located in a second container 2. This is maintained in constant movement by means of an agitator 3 and fed to a nozzle 5 through a tube 4 by a pump (not shown). It is sprayed onto the fluid bed through the nozzle 5. The final product is the tableting excipient of the invention. This may be used directly by a tablet producer in that it is to be mixed with the active substance of the tablet. This thereby requires only a single dosing procedure. The tableting excipient of the invention can also be stored and made available for future processing.

LIST OF REFERENCE SYMBOLS

1 Container for producing the fluid bed
1.1 Air intake
1.2 Air outlet
2 Container for receiving a lubricant
3 Agitator
4 Tube
5 Spray nozzle

The invention claimed is:

1. A tableting mixture, produced by a process comprising the steps of:
   (1) providing at least two components selected from the group consisting of a filler or binding agent; a flow regulating agent; and a disintegrant, wherein
      the filler or binding agent is selected from the group consisting of a cellulose, a cellulose derivative, a saccharide, and a polyol:
      the flow regulating agent is selected from the group consisting of silicon dioxide, calcium silicate, magnesium silicate, and aluminum silicate; and
      the disintegrant is selected from the group consisting of croscarmellose sodium, starch, sodium starch glycolate, cross-linked polyvinylpyrrolidone, soy polysaccharide, cyclodextrin, xylan, pectin, gelatin, polymethacrylic acid, and an ion exchange resin;
   (2) providing a sodium stearyl fumarate as a lubricant;
   (3) producing a granulate including the at least two components of step (1) and the sodium stearyl fumarate of step (2); and
   (4) after steps (1), (2), and (3), adding an active substance to the granulate of step (3);
      wherein the tableting mixture produced by performing step (4) after steps (1), (2), and (3) has better compressibility than a tableting mixture produced by performing steps (1) and (4) before step (2).

2. The tableting mixture according to claim 1, wherein step (3) comprises: forming a fluid bed from the at least two components of step (1); and spraying the sodium stearyl fumarate of step (2) onto or into the fluid bed formed from the at least two components of step (1).

3. The tableting mixture according to claim 1, wherein the filler or the binding agent comprises 59-98% of the granulate.

4. The tableting mixture according to claim 1, wherein the flow regulating agent comprises 1-20% of the granulate.

5. The tableting mixture according to claim 1, wherein the disintegrant comprises 0.5-15% of the granulate.

6. The tableting mixture according to claim 1, wherein step (3) is performed in a device with a container for receiving the at least two components of step (1);
   wherein the device is equipped for forming a fluid bed of one or more substances in the container; and
   wherein the device includes a feed device for supplying the sodium stearyl fumarate of step (2).

7. The tableting mixture according to claim 6, wherein the feed device contains a spray nozzle for spraying the sodium stearyl fumarate on or into the fluid bed.

8. The tableting mixture according to claim 6, wherein the container contains an intake for feeding and an output for discharging air or other gaseous substances.

9. The tableting mixture according to claim 1, wherein the filler or binding agent is selected from the groups consisting of:
   (i) microcrystalline cellulose, powdered cellulose, methyl cellulose, ethyl cellulose, hypromellose, and hydroxypropyl cellulose;
   (ii) lactose, glucose, sucrose, fructose, and combinations thereof;
   (iii) mannitol, sorbitol, xylitol, isomalt and combinations thereof.

10. A granulated tableting excipient consisting of a stearyl fumarate as a lubricant and at least two components selected from the group consisting of a filler or binding agent; a flow regulating agent; and a disintegrant; wherein the filler or binding agent is selected from the group consisting of a cellulose, a cellulose derivative, a saccharide, and a polyol:
the flow regulating agent is selected from the group consisting of silicon dioxide, calcium silicate, magnesium silicate, and aluminum silicate;
the disintegrant is selected from the group consisting of croscarmellose sodium, starch, sodium starch glycolate, cross-linked polyvinylpyrrolidone, soy polysaccharide, cyclodextrin, xylan, pectin, gelatin, polymethacrylic acid, and an ion exchange resin.

11. The granulated tableting excipient according to claim 10, wherein the filler or a binding agent is present in an amount of from 59% to 98% by weight of the granulate.

12. The granulated tableting excipient according to claim 11, wherein the flow regulating agent is present in an amount of from 1% to 20% by weight of the granulate.

13. The granulated tableting excipient according to claim 11, wherein the disintegrant is present in an amount of from 0.5% to 15% of by weight of the granulate.

14. The tableting excipient according to claim 10, wherein the lubricant comprises a sodium stearyl fumarate.

* * * * *